(12) United States Patent
Auguste et al.

(10) Patent No.: US 9,211,243 B2
(45) Date of Patent: Dec. 15, 2015

(54) COSMETIC COMPOSITION COMPRISING AT LEAST ONE VOLATILE ESTER

(75) Inventors: Frédéric Auguste, Chevilly-Larue (FR); Jean-Yves Fouron, Bourg la Reine (FR)

(73) Assignee: L'OREAL, Paris (FR)

( * ) Notice: Subject to any disclaimer, the term of this patent is extended or adjusted under 35 U.S.C. 154(b) by 1046 days.

(21) Appl. No.: 11/984,725

(22) Filed: Nov. 21, 2007

(65) Prior Publication Data

US 2008/0138302 A1 Jun. 12, 2008

Related U.S. Application Data

(60) Provisional application No. 60/872,777, filed on Dec. 5, 2006.

(30) Foreign Application Priority Data

Nov. 23, 2006 (FR) .................. 06 55073

(51) Int. Cl.
| | | |
|---|---|---|
| A61K 8/37 | (2006.01) | |
| A61Q 19/00 | (2006.01) | |
| A61Q 17/04 | (2006.01) | |
| A61Q 1/14 | (2006.01) | |
| A61Q 5/02 | (2006.01) | |
| A61Q 5/06 | (2006.01) | |
| A61Q 5/00 | (2006.01) | |
| A61Q 1/06 | (2006.01) | |
| A61Q 19/10 | (2006.01) | |
| C11D 3/20 | (2006.01) | |
| A61Q 1/02 | (2006.01) | |
| A61Q 15/00 | (2006.01) | |

(52) U.S. Cl.
CPC . *A61K 8/37* (2013.01); *A61Q 19/00* (2013.01); *A61Q 1/02* (2013.01); *A61Q 1/06* (2013.01); *A61Q 1/14* (2013.01); *A61Q 15/00* (2013.01); *A61Q 17/04* (2013.01)

(58) Field of Classification Search
CPC ............ A61K 8/37; A61Q 1/02; A61Q 1/06; A61Q 19/00; A61Q 15/00; A61Q 17/04; A61Q 1/14
See application file for complete search history.

(56) References Cited

U.S. PATENT DOCUMENTS

| | | | |
|---|---|---|---|
| 2,216,485 A | 10/1940 | Brandt | |
| 4,009,253 A | 2/1977 | Schleppnik et al. | |
| 4,009,254 A | 2/1977 | Renold | |
| 4,126,585 A | 11/1978 | Conrad et al. | |
| 4,187,251 A | 2/1980 | Schleppnik | |
| 4,217,250 A | 8/1980 | Holzner | |
| 4,447,365 A | 5/1984 | Boden et al. | |
| 4,515,711 A | 5/1985 | Chalk et al. | |
| 5,814,163 A | 9/1998 | Wojcik | |
| 5,879,690 A * | 3/1999 | Perricone | 424/401 |
| 5,883,058 A | 3/1999 | Wells et al. | |
| 5,895,644 A | 4/1999 | Albanese et al. | |
| 6,403,070 B1 | 6/2002 | Pataut et al. | |
| 6,506,243 B1 | 1/2003 | Yezrielev et al. | |
| 6,534,072 B2 | 3/2003 | Mondet et al. | |
| 2002/0160066 A1 | 10/2002 | Majeed et al. | |
| 2003/0017124 A1 | 1/2003 | Agostini et al. | |
| 2003/0092599 A1 | 5/2003 | Suganuma et al. | |
| 2003/0180374 A1 | 9/2003 | Corbella et al. | |
| 2003/0191045 A1 | 10/2003 | Ansari et al. | |
| 2004/0161395 A1* | 8/2004 | Patil et al. | 424/70.12 |
| 2004/0221858 A1 | 11/2004 | Higashi et al. | |
| 2005/0079986 A1 | 4/2005 | Mitchell et al. | |
| 2006/0166857 A1 | 7/2006 | Surburg et al. | |
| 2007/0053862 A1 | 3/2007 | Touboul et al. | |
| 2009/0018051 A1 | 1/2009 | Reckziegel et al. | |

FOREIGN PATENT DOCUMENTS

| | | |
|---|---|---|
| DE | 41 19 890 | 12/1992 |
| EP | 0 104 602 | 4/1984 |
| EP | 0 227 108 | 7/1987 |
| EP | 0 368 406 | 5/1990 |
| EP | 0 542 669 A1 | 5/1993 |
| EP | 0 787 730 A1 | 8/1997 |
| EP | 0 787 731 A2 | 8/1997 |

(Continued)

OTHER PUBLICATIONS

Clearco Product Information: Cyclo-2245 (D5) Cyclomethicone Fluid; [online] retrieved from http://www.clearcoproducts.com on Apr. 1, 2010; 1 page.*
English language abstract EP 0 787 730.
English language abstract EP 0 787 731.
English language Patent Abstracts of Japan JP 01104004 A.
French Search Report for FR0655073 (French priority application for the present application) dated Jun. 26, 2007.
Chemical Abstracts, vol. 54, No. 2, Jan. 25, 1960, Columbus, OH, US.
Co-pending U.S. Appl. No. 11/984,726, filed Nov. 21, 2007.
Database WPI week 198933, Derwent Publications Ltd., London, GB; 1989-237690.

(Continued)

*Primary Examiner* — Johann R Richter
*Assistant Examiner* — Genevieve S Alley
(74) *Attorney, Agent, or Firm* — Oblon, McClelland, Maier & Neustadt, L.L.P.

(57) ABSTRACT

The present application relates to a cosmetic composition comprising at least one ester corresponding to formula (I) below:

$$R1COOR2 \qquad (I)$$

in which R1 represents H or a linear or branched hydrocarbon-based radical, and R2 represents a linear or branched hydrocarbon-based radical, with the proviso that:
  when R2 is a linear hydrocarbon-based radical and R1 is H or a linear hydrocarbon-based radical, then $7 \leq R1+R2 \leq 8$; and
  when at least one of R1 and R2 is a branched hydrocarbon-based radical, then $8 \leq R1+R2 \leq 10$, with the proviso that, when R1 is tert-butyl, then R2 is not isohexyl.

This composition can be used as a product for caring for and/or making up keratin materials, in particular the skin, the lips and/or the integuments.

31 Claims, No Drawings

(56) References Cited

FOREIGN PATENT DOCUMENTS

| | | |
|---|---|---|
| EP | 1 229 032 A2 | 8/2002 |
| EP | 1 238 650 | 9/2002 |
| EP | 1 297 854 | 4/2003 |
| EP | 1 512 392 | 3/2005 |
| EP | 1 554 938 A1 | 7/2005 |
| EP | 1 787 689 | 5/2007 |
| GB | 2 422 780 | 8/2006 |
| JP | 61-289019 | 12/1986 |
| JP | 01-104004 A | 4/1989 |
| JP | 02-191214 | 7/1990 |
| JP | 8-333599 | 12/1996 |
| JP | 09-249520 | 9/1997 |
| JP | 2001-247440 | 9/2001 |
| JP | 2003-137758 | 5/2003 |
| JP | 2005-533779 | 11/2005 |
| WO | WO 96/08537 | 3/1996 |
| WO | WO 99/20127 | 4/1999 |
| WO | WO 01/85130 | 11/2001 |
| WO | WO 02/05759 | 1/2002 |
| WO | WO 02/39971 | 5/2002 |
| WO | WO 02/100372 | 12/2002 |
| WO | WO 03/045339 | 6/2003 |
| WO | WO 03/105789 | 12/2003 |
| WO | WO 2004/060332 | 7/2004 |
| WO | WO 2004/078154 | 9/2004 |
| WO | WO 2004/082656 | 9/2004 |
| WO | WO 2005/004825 | 1/2005 |
| WO | WO 2006/013413 | 2/2006 |
| WO | WO 2006/124230 | 11/2006 |
| WO | WO 2007/017478 | 2/2007 |

OTHER PUBLICATIONS

English language Abstract of DE 41 19 890, dated Dec. 24, 1992.
English language Abstract of JP 8-333599, dated Dec. 17, 1996.
French Search Report for FR 06/55063, dated Jul. 11, 2007.
French Search Report for FR 06/55069, dated Oct. 23, 2007.
French Search Report for FR 06/55071, dated Jul. 6, 2007.
French Search Report for FR 06/55074, dated Jun. 25, 2007.
Office Action mailed Jan. 28, 2010, in co-pending U.S. Appl. No. 11/984,726.
Office Action mailed Jul. 10, 2009, in co-pending U.S. Appl. No. 11/984,726.
Office Action issued May 7, 2013, in corresponding Japanese Patent Application 2007-302821 (English Translation).
Decision of Rejection issued May 27, 2014 in Japanese Patent Application No. 2007-302821(submitting English translation only).
Decision to Dismiss the Amendments issued May 27, 2014 in Japanese Patent Application No. 2007-302821(submitting English translation only).

* cited by examiner

COSMETIC COMPOSITION COMPRISING AT LEAST ONE VOLATILE ESTER

This application claims benefit of U.S. Provisional Application No. 60/872,777, filed Dec. 5, 2006, the contents of which are incorporated herein by reference. This application also claims benefit of priority under 35 U.S.C. §119 to French Patent Application No. FR 0655073, filed Nov. 23, 2006, the contents of which are also incorporated herein by reference.

The present invention relates to a cosmetic composition, in particular a cosmetic composition for making up or caring for the skin of the human face or body, the scalp, the lips or the integuments, such as the hair, the eyelashes, the eyebrows or the nails.

The composition of the invention can in particular constitute a care product, a hairstyling product or a make-up product for the lips, the body or the integuments that may also have care properties. The composition of the invention may in particular constitute a lipstick or a lip gloss, a face powder or an eye shadow, a tattoo product, a mascara, an eyeliner, an artificial skin-tanning product, a foundation or a care cream.

Cosmetic compositions must generally have certain properties such as staying power, migration resistance, transfer resistance, play-time, slip on application (or good spreading), comfort, sheen or coverage. The same composition does not necessarily have to have all these properties; however, in the majority of cases, it is desired for the composition to have at least some of them.

The staying power of the composition may in particular be the staying power with respect to water or to rubbing by the fingers, or alternatively with respect to tears, sweat or sebum.

The migration-resistance property corresponds, as far as the composition is concerned, to it not migrating into the folds of the skin, such as the wrinkles or fine lines located around the lips and the eyes (eyelids in particular).

The transfer-resistance characteristic of a composition corresponds to the fact that, once applied, it does not become notably deposited on the surfaces with which it comes into contact (glass, cup, cigarette, clothing, for example).

The play-time of a product corresponds to the time for which the consumer may work said product when applying it, and therefore reflects the ease with which the product is applied.

Cosmetic compositions commonly comprise a fatty phase containing a volatile solvent. In fact, said solvent makes it possible to bring about a change in the properties of the product during and after deposition, thereby resulting, depending on the cosmetic product envisaged, in properties of staying power of the deposited product, or of comfort or texture during application of the product, and also in specific mechanical or optical properties of the deposits.

These volatile solvents are conventionally used in the care, hygiene, hair product, fragrance and make-up fields, in very varied galenical forms: direct or inverse emulsions, anhydrous pastes, anhydrous sticks, solid emulsions, etc.

In the context of the formulation of cosmetic compositions, it would be advantageous to have novel volatile solvents which make it possible to obtain compositions having at least some of the properties stated above.

The Applicant has discovered, unexpectedly, that a specific category of compounds meets the criteria stated above and thus confers on the compositions excellent cosmetic properties such as good spreading and/or a non-greasy feel and/or comfort and/or transfer resistance and/or migration resistance, for example. This list is not exhaustive and, more generally, these compounds exhibit good compatibility with other constituents normally present in cosmetic compositions and confer most of the conventionally desired properties on the composition.

More specifically, a subject of the invention is a cosmetic composition comprising, in a physiologically acceptable medium, at least one ester corresponding to formula (I) below:

$$R1COOR2 \quad (I)$$

in which R1 represents a hydrogen atom H or a linear or branched hydrocarbon-based radical, and R2 represents a linear or branched hydrocarbon-based radical, with the proviso that:
  when R2 is a linear hydrocarbon-based radical and R1 is H or a linear hydrocarbon-based radical, then $7 \leq R1+R2 \leq 8$; and
  when at least one of R1 and R2 is a branched hydrocarbon-based radical, then $8 \leq R1+R2 \leq 10$,
and with the proviso that, when R1 is tert-butyl, then R2 is not isohexyl.

The expression "$7 \leq R1+R2 \leq 8$" means that the sum of the carbon atoms of R1 and R2 is between 7 and 8. Similarly, "$8 \leq R1+R2 \leq 10$" means that the sum of the carbon atoms of R1 and R2 is between 8 and 10.

Another subject of the invention is a cosmetic composition comprising, in a physiologically acceptable medium, at least one ester corresponding to formula (I) below:

$$R1COOR2 \quad (I)$$

in which R1 represents H or a linear or branched hydrocarbon-based radical, and R2 represents a linear or branched hydrocarbon-based radical, with the proviso that:
  when R2 is a linear hydrocarbon-based radical and R1 is H or a linear hydrocarbon-based radical, then $7 \leq R1+R2 \leq 8$; and
  when at least one of R1 and R2 is a branched hydrocarbon-based radical, then $8 \leq R1+R2 \leq 10$,
and with the proviso that, neither of R1 and R2 comprises a quaternary carbon (i.e. the ester of formula (I) does not comprise a quaternary carbon).

A subject of the invention is also a cosmetic composition comprising, in a physiologically acceptable medium, at least one ester corresponding to formula (I) below:

$$R1COOR2 \quad (I)$$

in which R1 represents H or a linear or branched hydrocarbon-based radical, and R2 represents a linear or branched hydrocarbon-based radical, with the proviso that:
  when R2 is a linear hydrocarbon-based radical and R1 is H or a linear hydrocarbon-based radical, then $7 \leq R1+R2 \leq 8$; and
  when at least one of R1 and R2 is a branched hydrocarbon-based radical, then $8 \leq R1+R2 \leq 10$,
and with the proviso that said ester of formula (I) comprises no more than two branches, or better still, no more than one branch.

The term "hydrocarbon-based" is intended to mean a radical or a compound formed essentially of or even consisting of carbon and hydrogen atoms, and optionally of oxygen, nitrogen, sulphur or phosphorus atoms, and containing no silicon or fluorine atoms. It may contain alcohol, ether, carboxylic acid, amine and/or amide groups. Preferably, the adjective "hydrocarbon-based" denotes a radical or a compound consisting only of carbon and hydrogen atoms, such as alkyl, alkenyl or alkynyl radicals, for example.

Preferably, the composition according to the invention is a cosmetic composition for making up or caring for keratin materials.

In the context of the present invention, the term "keratin materials" comprises the skin, the lips, the nails, the hair, the eyelashes and the eyebrows, and the term "keratin fibres" comprises the hair, the eyelashes and the eyebrows.

A preferred formula of the esters of the compositions according to the invention are the esters of formula II

R1COOR2     (II)

in which R1 represents H or a linear or branched hydrocarbon-based radical, and R2 represents a linear or branched hydrocarbon-based radical, with the proviso that:
when R2 is a linear hydrocarbon-based radical and R1 is H or a linear hydrocarbon-based radical, then 7≤R1+R2≤8; and
when at least one of R1 and R2 is a branched hydrocarbon-based radical, then 8≤R1+R2≤9.

In the various formulae mentioned above, R1 and R2 are chosen independently of one another and are two distinct radicals, i.e. they are not linked to one another by a covalent bond.

The expression "the ester of formula (I)" or "the ester" covers the case where it is a question of one or more individual compounds and also a mixture thereof (idem in the case of the esters of formula (II)). Thus, this expression covers "at least one ester of formula (I)".

Preferably, for formulae (I) and (II), R1 is H or an aliphatic hydrocarbon-based radical and R2 is an aliphatic hydrocarbon-based radical.

Advantageously, R1 and R2 are alkyl radicals.

According to a first embodiment of the invention, R2 is a linear hydrocarbon-based radical and R1 is H or a linear hydrocarbon-based radical. Among these esters, mention may be made of:

Linear esters containing 8 carbon atoms, such as
pentyl propanoate,
ethyl hexanoate,
heptyl formate,
butyl butanoate,
methyl heptanoate,
hexyl acetate, and
propyl pentanoate.
Linear esters containing 9 carbon atoms, such as
ethyl heptanoate,
methyl octanoate,
heptyl acetate,
octyl formate,
hexyl propanoate,
pentyl butanoate,
butyl pentanoate, and
propyl hexanoate.

According to a second embodiment of the invention, R1 and/or R2 are branched. The term "branched structure" should be understood to mean that the esters have at least one branch, of minimum length corresponding to a methyl group —CH$_3$. In other words, esters having in total at least 3 -CH$_3$ groups over the molecule as a whole are considered to be branched. More generally, the number of branches of a molecule corresponds to the number of side groups containing at least one carbon atom and branched on the main chain of the molecule, the main chain corresponding to the longest carbon chain of the molecule (see Organic Chemistry, S. H. Pine, 5th Edition; McGraw-Hill, Chapter 3).

It is thus envisaged, according to different variants of the invention, that only R1 or only R2 is branched, or else that R1 and R2 are both branched.

Advantageously, the esters of formula (I) or of formula (II) comprise no more than 4 branches, or better still no more than 2 or 3 branches.

More preferably, the esters of formula (I) or of formula (II) comprise no more than one branch.

The number of branches corresponds to the number of —CH$_3$ groups on the entire molecule, minus two. Thus, for example, butanoic acid, 2,2-dimethyl, pentyl ester has four —CH$_3$ groups on the entire molecule and therefore has two branches. It will be noted that the number of branches does not therefore necessarily correspond to the number of branched carbons. In the molecule mentioned above as an example, there is in fact only one branched carbon, but two branches.

Preferably, R1 and/or R2 do (does) not comprise a quaternary carbon. The term "quaternary carbon" is intended to mean a carbon that does not bear a hydrogen atom and is bonded to four other carbon atoms.

Among the branched esters containing 9 carbon atoms, mention may be made of:
Hexanoic acid, 5-methyl-, ethyl ester;
Pentanoic acid, 2-methylpropyl ester;
Butanoic acid, 3-methylbutyl ester;
Pentanoic acid, 1-methylpropyl ester;
Butanoic acid, 1-methylbutyl ester;
Butanoic acid, 1-methylbutyl ester;
Butanoic acid, 1-ethylpropyl ester;
Hexanoic acid, 3-methyl-, ethyl ester;
Butanoic acid, 2-methylbutyl ester;
Hexanoic acid, 2-ethyl-, methyl ester;
Butanoic acid, 2-methylbutyl ester;
Hexanoic acid, 4-methyl-, ethyl ester;
Butanoic acid, 2-methyl-, butyl ester;
Hexanoic acid, 2-methyl-, ethyl ester;
Hexanoic acid, 4-methyl-, ethyl ester;
Heptanoic acid, 4-methyl-, methyl ester;
Hexanoic acid, 3-ethyl-, methyl ester;
Hexanoic acid, 3-methyl-, ethyl ester-;
Pentanoic acid, 2-propyl-, methyl ester;
Hexanoic acid, 1-methylethyl ester;
Pentanoic acid, 1-methylpropyl ester;
Propanoic acid, 2-methyl-, pentyl ester;
Heptanoic acid, 6-methyl-, methyl ester;
Pentanoic acid, 4-methyl-, propyl ester;
Hexanoic acid, 4-ethyl-, methyl ester;
Hexanoic acid, 2-methyl-, ethyl ester;
Hexanoic acid, 3-ethyl-, methyl ester;
Pentanoic acid, 3-methyl-, propyl ester;
Heptanoic acid, 4-methyl-, methyl ester;
Hexanoic acid, 2-methyl-, ethyl ester;
Hexanoic acid, 3-methyl-, ethyl ester;
Heptanoic acid, 5-methyl-, methyl ester;
Hexanoic acid, 3-ethyl-, methyl ester;
Pentanoic acid, 2-ethyl-, ethyl ester;
Butanoic acid, 2-methylbutyl ester;
Heptanoic acid, 2-methyl-, methyl ester;
Butanoic acid, 2-ethyl-, propyl ester;
Pentanoic acid, 3-methyl-, propyl ester;
Formic acid, 2-ethylhexyl ester;
Butanoic acid, 1-methylbutyl ester;
Hexanoic acid, 4-methyl-, ethyl ester-;
Pentanoic acid, 2-methyl-, propyl ester;
Heptanoic acid, 3-methyl-, methyl ester;
Butanoic acid, 2-methyl-, butyl ester-;
Butanoic acid, 2-methyl-, butyl ester;
Pentanoic acid, 3-ethyl-, ethyl ester;
Hexanoic acid, 2-ethyl-, methyl ester;

Heptanoic acid, 5-methyl-, methyl ester;
Propionic acid, 2-ethylbutyl ester;
Heptanoic acid, 3-methyl-, methyl ester-;
Heptanoic acid, 3-methyl-, methyl ester.

Among the branched esters containing 10 carbon atoms, mention may be made of:
Octanoic acid, 6-methyl-, methyl ester;
Heptanoic acid, 3-methyl-, ethyl ester;
Acetic acid, 2-ethylhexyl ester;
Valeric acid, 3-methyl-, sec-butyl ester;
Hexanoic acid, 2-methylpropyl ester-;
Heptanoic acid, 2-methyl-, ethyl ester-;
Butanoic acid, 1-methylpentyl ester;
Hexanoic acid, 1-methylpropyl ester;
Hexanoic acid, 1-methylpropyl ester;
Butanoic acid, 1-methylpentyl ester;
Butanoic acid, 1-ethylbutyl ester;
Butanoic acid, 1-ethylbutyl ester;
Butanoic acid, 1-ethylbutyl ester;
Octanoic acid, 3-methyl-, methyl ester;
Heptanoic acid, 5-methyl-, ethyl ester;
Butanoic acid, 2-methyl-, pentyl ester;
Butanoic acid, 2-methyl-, pentyl ester;
Octanoic acid, 3-methyl-, methyl ester;
Octanoic acid, 4-methyl-, methyl ester;
Octanoic acid, 5-methyl-, methyl ester;
Octanoic acid, 3-methyl-, methyl ester;
Heptanoic acid, 4-methyl-, ethyl ester;
Heptanoic acid, 2-methyl-, ethyl ester;
Pentanoic acid, 2-propyl-, ethyl ester;
Acetic acid, 2-ethylhexyl ester;
Pentanoic acid, 2-methyl, butyl ester;
Pentanoic acid, 4-methyl-, butyl ester;
Pentanoic acid, 3-methylbutyl ester;
Octanoic acid, 2-methyl-, methyl ester;
Heptanoic acid, 4-methyl-, ethyl ester;
Octanoic acid, 4-methyl-, methyl ester;
Octanoic acid, 4-methyl-, methyl ester;
Octanoic acid, 2-methyl-, methyl ester;
Propanoic acid, 2-methyl-, hexyl ester;
Butanoic acid, 3-methyl-, pentyl ester;
Hexanoic acid, 2-ethyl-, ethyl ester;
Acetic acid, isooctyl ester;
Acetic acid, isooctyl ester;
Pivalic acid, 2-methylbutyl ester;
Heptanoic acid, 1-methylethyl ester;
1-Heptanol, 6-methyl-, acetate;
Isooctanoic acid, ethyl ester;
Isooctanoic acid, ethyl ester;
Hexanoic acid, 2-ethyl-, ethyl ester;
Hexanoic acid, 2-ethyl-, ethyl ester;
Heptanoic acid, 3-methyl-, ethyl ester;
Heptanoic acid, 5-methyl-, ethyl ester;
Heptanoic acid, 2-methyl-, ethyl ester;
Pentanoic acid, 3-methyl-, butyl ester;
Heptanoic acid, 3-ethyl-, methyl ester;
Pentanoic acid, 2-ethyl-, propyl ester;
Acetic acid, 2-ethylhexyl ester;
Butanoic acid, 2-ethyl-, butyl ester;
Octanoic acid, 7-methyl-, methyl ester;
Octanoic acid, 6-methyl-, methyl ester;
Hexanoic acid, 2-propyl-, methyl ester;
Pentanoic acid, 3-methyl-, butyl ester;
Acetic acid, sec-octyl ester;
Acetic acid, sec-octyl ester;
Pentanoic acid, 2-methylbutyl ester;
Hexanoic acid, 4-methyl-, propyl ester;
Heptanoic acid, 6-methyl-, ethyl ester;
Pentanoic acid, 2-methyl-, butyl ester;
Heptanoic acid, 3-ethyl-, methyl ester;
Heptanoic acid, 5-methyl-, ethyl ester;
Formic acid, isononyl ester;
Formic acid, isononyl ester;
Octanoic acid, 2-methyl-, methyl ester;
Butanoic acid, 2-methyl-, pentyl ester;
Butanoic acid, 1-methylpentyl ester;
Hexanoic acid, 3-propyl-, methyl ester;
Butanoic acid, 2-ethylbutyl ester;
Heptanoic acid, 2-ethyl-, methyl ester;
Hexanoic acid, 1-methylpropyl ester;
Butanoic acid, 4-methylpentyl ester;
Butanoic acid, 3-methylpentyl ester;
Hexanoic acid, 3-ethyl-, ethyl ester;
Pentanoic acid, 1-methylbutyl ester;
Isononanoic acid, methyl ester;
Hexanoic acid, 4-ethyl-, ethyl ester;
Heptanoic acid, 3,3-dimethyl-, methyl ester;
Hexanoic acid, 5,5-dimethyl-, ethyl ester;
Heptanoic acid, 2,3-dimethyl-, methyl ester;
Heptanoic acid, 2,3-dimethyl-, methyl ester;
Butanoic acid, 2-methyl-, 2-methylbutyl ester;
Heptanoic acid, 2,3-dimethyl-, methyl ester;
Hexanoic acid, 3,3-dimethyl-, ethyl ester;
Pentanoic acid, 1,1-dimethylpropyl ester;
Butanoic acid, 3-methyl-, 1-methylbutyl ester;
Hexanoic acid, 4,4-dimethyl-, ethyl ester;
Pentanoic acid, 3-ethyl-2-methyl-, ethyl ester;
Pentanoic acid, 2-ethyl-3-methyl-, ethyl ester;
Butanoic acid, 2-methyl-, 3-methylbutyl ester;
Butanoic acid, 2-methyl-, 3-methylbutyl ester;
Heptanoic acid, 2,4-dimethyl-, methyl ester;
Heptanoic acid, 2,4-dimethyl-, methyl ester;
Pentanoic acid, 2-ethyl-2-methyl-, ethyl ester-;
Heptanoic acid, 2,4-dimethyl-, methyl ester;
Heptanoic acid, 5,6-dimethyl-, methyl ester;
Propanoic acid, 2,2-dimethyl-, pentyl ester;
Pentanoic acid, 2,2-dimethylpropyl ester;
Butanoic acid, 3-methyl-, 2-methylbutyl ester;
Butanoic acid, 2-methyl-, 2-methylbutyl ester;
Heptanoic acid, 3,5-dimethyl-, methyl ester;
Hexanoic acid, 1,1-dimethylethyl ester;
Pentanoic acid, 4-methyl-, 2-methylpropyl ester;
Butanoic acid, 2-methyl-, 3-methylbutyl ester;
Heptanoic acid, 3,4-dimethyl-, methyl ester;
Heptanoic acid, 3,4-dimethyl-, methyl ester;
Hexanoic acid, 2-ethyl-2-methyl-, methyl ester;
Heptanoic acid, 2,6-dimethyl-, methyl ester;
Butanoic acid, 2,2-diethyl-, ethyl ester;
Propanoic acid, 2-methyl-, 4-methylpentyl ester;
Hexanoic acid, 2,2-dimethyl-, ethyl ester;
Heptanoic acid, 2,5-dimethyl-, methyl ester;
Hexanoic acid, 2-ethyl-4-methyl-, methyl ester;
Heptanoic acid, 2,5-dimethyl-, methyl ester;
Hexanoic acid, 2-ethyl-4-methyl-, methyl ester;
Hexanoic acid, 2-methyl-, 1-methylethyl ester;
Heptanoic acid, 5,5-dimethyl-, methyl ester;
Heptanoic acid, 4,4-dimethyl-, methyl ester;
Hexanoic acid, 3-ethyl-3-methyl-, methyl ester;
Butanoic acid, 2,2-dimethyl-, butyl ester;
Butanoic acid, 1,3-dimethylbutyl ester;
Pentanoic acid, 2-methyl-2-propyl-, methyl ester;
Hexanoic acid, 2-ethyl-2-methyl-, methyl ester;
Pentanoic acid, 2-ethyl-, 1-methylethyl ester;
Butanoic acid, 2-methyl-, 1-methylbutyl ester;

Pentanoic acid, 2-methyl-, 1-methylpropyl ester;
Pentanoic acid, 2,2-dimethyl-, propyl ester;
Butanoic acid, 3-methyl-, 1-methylbutyl ester;
Butanoic acid, 3-methyl-, 1-methylbutyl ester;
Hexanoic acid, 2,4-dimethyl-, ethyl ester;
Heptanoic acid, 2,6-dimethyl-, methyl ester;
Hexanoic acid, 4-methyl-, 1-methylethyl ester;
Pentanoic acid, 2-methyl-, 2-methylpropyl ester;
Hexanoic acid, 3,5-dimethyl-, ethyl ester;
Heptanoic acid, 2,6-dimethyl-, methyl ester;
Pentanoic acid, 3-ethyl-4-methyl-, ethyl ester;
Butanoic acid, 3-methyl-, 3-methylbutyl ester;
Butanoic acid, 2-ethyl-, 2-methylpropyl ester;
Butanoic acid, 2-ethyl-, 1-methylpropyl ester;
Propanoic acid, 2-methyl-, 2-ethylbutyl ester;
Butanoic acid, 2-methyl-, 1-methylbutyl ester;
Butanoic acid, 2-methyl-, 1-methylbutyl ester;
Pentanoic acid, 3,3-diethyl-, methyl ester;
Hexanoic acid, 4,5-dimethyl-, ethyl ester;
Butanoic acid, 2-methyl-, 2-methylbutyl ester;
Butanoic acid, 2-methyl-, 2-methylbutyl ester-;
Heptanoic acid, 2,2-dimethyl-, methyl ester;
Pentanoic acid, 2-ethyl-2-methyl-, ethyl ester;
Hexanoic acid, 3,5-dimethyl-, ethyl ester;
Hexanoic acid, 3,5-dimethyl-, ethyl ester;
Propanoic acid, 2-methyl-, 2-methylpentyl ester;
Propanoic acid, 2-methyl-, 3-methylpentyl ester;
Hexanoic acid, 3,4-dimethyl-, ethyl ester;
Pentanoic acid, 3-ethyl-3-methyl-, ethyl ester;
Butanoic acid, 3,3-dimethyl-, butyl ester;
Butyric acid, 2,3-dimethyl-, butyl ester;
Hexanoic acid, 2,3-dimethyl-, ethyl ester;
Hexanoic acid, 2-isopropyl-, methyl ester;
Heptanoic acid, 3,6-dimethyl-, methyl ester;
Valeric acid, 3,3-dimethyl-, propyl ester;
Hexanoic acid, 2,3,5-trimethyl-, methyl ester;
Valeric acid, 2,2,3-trimethyl-, ethyl ester;
Pentanoic acid, 3,4,4-trimethyl-, ethyl ester;
Butanoic acid, 2,2-diethyl-3-methyl-, methyl ester;
Butanoic acid, 2-methyl-, 1,1-dimethylpropyl ester;
Butanoic acid, 2-methyl-, 2,2-dimethylpropyl ester;
Pentanoic acid, 2,4-dimethyl-, 1-methylethyl ester;
tert-Nonanoic acid, methyl ester;
tert-Nonanoic acid, methyl ester;
Pentanoic acid, 2-methyl-, 1,1-dimethylethyl ester;
Butyric acid, 2,2-dimethyl-, isobutyl ester;
Pentanoic acid, 4-methyl-2-(1-methylethyl)-, methyl ester;
Propanoic acid, 2-methyl-, 1,1-dimethylbutyl ester;
Pentanoic acid, 4-methyl-, 1,1-dimethylethyl ester;
Propanoic acid, 2,2-dimethyl-, 3-methylbutyl ester;
Butanoic acid, 3-methyl-, 2,2-dimethylpropyl ester;
Butanoic acid, 3,3-dimethyl-, 1-methylpropyl ester;
Butanoic acid, 3-methyl-, 1,1-dimethylpropyl ester;
Butanoic acid, 2-ethyl-, 1,1-dimethylethyl ester;
Pentanoic acid, 2,2-dimethyl-, 1-methylethyl ester;
Butanoic acid, 2-ethyl-2-methyl-, 1-methylethyl ester;
Pentanoic acid, 2,4,4-trimethyl-, ethyl ester;
Hexanoic acid, 2,2,4-trimethyl-, methyl ester;
Pentanoic acid, 2-ethyl-2,3-dimethyl-, methyl ester;
Hexanoic acid, 2,2,5-trimethyl-, methyl ester;
Butanoic acid, 3-methyl-2-(1-methylethyl)-, ethyl ester;
Butanoic acid, 2-ethyl-3,3-dimethyl-, ethyl ester;
Pentanoic acid, 2,3,4-trimethyl-, ethyl ester;
Pentanoic acid, 2-ethyl-4,4-dimethyl-, methyl ester;
Hexanoic acid, 2,3,4-trimethyl-, methyl ester;
Hexanoic acid, 3,5,5-trimethyl-, methyl ester;
Pentanoic acid, 3,3,4-trimethyl-, ethyl ester;
Butanoic acid, 2-methyl-, 1,2-dimethylpropyl ester;
Butanoic acid, 1,2,2-trimethylpropyl ester;
Pentanoic acid, 2,2,4-trimethyl-, ethyl ester;
Pentanoic acid, 3,4,4-trimethyl-, ethyl ester;
Pentanoic acid, 3,4,4-trimethyl-, ethyl ester;
Pentanoic acid, 2-ethyl-3,3-dimethyl-, methyl ester;
Butyric acid, 2-ethyl-2,3-dimethyl-, ethyl ester;
Hexanoic acid, 3,3,5-trimethyl-, methyl ester;
Butanoic acid, 3,3-dimethyl-, 2-methylpropyl ester;
Valeric acid, 3,3-dimethyl-, isopropyl ester;
Propanoic acid, 2,2-dimethyl-, 2,2-dimethylpropyl ester.

Among the branched esters containing 11 carbon atoms, mention may be made of:
Butanoic acid, 3-methyl-, hexyl ester;
Butanoic acid, 2-methyl-, hexyl ester;
Pentanoic acid, 2-propyl-, propyl ester;
Pentanoic acid, 3-methylpentyl ester;
Butanoic acid, 1-methylhexyl ester;
Butanoic acid, 1-methylhexyl ester;
Hexanoic acid, 1-methylbutyl ester;
Hexanoic acid, 1-methylbutyl ester;
Heptanoic acid, 1-methylpropyl ester;
Butanoic acid, 1-ethylpentyl ester;
Butanoic acid, 1-ethylpentyl ester;
Hexanoic acid, 2-methyl-, butyl ester;
Hexanoic acid, 4-methyl-, butyl ester;
Octanoic acid, 3-methyl-, ethyl ester;
Hexanoic acid, 2-methyl-, butyl ester;
Butanoic acid, 2-methylhexyl ester;
Butanoic acid, 2-methyl-, hexyl ester;
Butanoic acid, 2-methyl-, hexyl ester;
Nonanoic acid, 3-methyl-, methyl ester;
Hexanoic acid, 2-propyl-, ethyl ester;
Octanoic acid, 2-methyl-, ethyl ester;
Octanoic acid, 6-methyl-, ethyl ester;
Octanoic acid, 4-methyl-, ethyl ester;
Octanoic acid, 2-ethyl-, methyl ester;
Octanoic acid, 4-methyl-, ethyl ester;
Hexanoic acid, 2-ethyl-, propyl ester;
Octanoic acid, 2-methyl-, ethyl ester;
Pentanoic acid, 2-methyl-, pentyl ester;
Hexanoic acid, 3-methyl-, butyl ester;
Nonanoic acid, 3-methyl-, methyl ester;
Hexanoic acid, 3-methylbutyl ester;
Propanoic acid, 2-methyl-, heptyl ester;
Octanoic acid, 6-methyl-, ethyl ester;
Octanoic acid, 3-ethyl-, methyl ester;
Hexanoic acid, 2-butyl-, methyl ester;
Pentanoic acid, 4-methyl-, pentyl ester;
Hexanoic acid, 2-methylbutyl ester;
Butanoic acid, 1-ethylpentyl ester;
Octanoic acid, 7-methyl-, ethyl ester;
Octanoic acid, 2-methyl-, ethyl ester;
Pentanoic acid, 4-methylpentyl ester;
Butanoic acid, 1-methylhexyl ester;
Pentanoic acid, 3-methyl-, pentyl ester;
Pentanoic acid, 2-ethyl-, butyl ester;
Butanoic acid, 2-ethyl-, pentyl ester;
Nonanoic acid, 8-methyl-, methyl ester;
Nonanoic acid, 7-methyl-, methyl ester;
Pentanoic acid, 3-methyl-, pentyl ester;
Hexanoic acid, 1-ethylpropyl ester;
Octanoic acid, 1-methylethyl ester;
Hexanoic acid, 2-methylbutyl ester;
Octanoic acid, 4-methyl-, ethyl ester;
Heptanoic acid, 2-propyl-, methyl ester;
Nonanoic acid, 2-methyl-, methyl ester;

Heptanoic acid, 2-ethyl-, ethyl ester;
Hexanoic acid, 4-methyl-, butyl ester;
Propanoic acid, 2-ethylhexyl ester;
Pentanoic acid, 2-methyl-, pentyl ester;
Heptanoic acid, 5-methyl-, propyl ester;
Octanoic acid, 4-ethyl-, methyl ester;
Pentanoic acid, 1-methylpentyl ester;
Heptanoic acid, 2-methylpropyl ester;
Caprylic acid, ε-methyl-, ethyl ester;
Butyric acid, 4-methyl-3-hexyl ester;
Nonanoic acid, 3-methyl-, methyl ester;
Hexanoic acid, 1-methylbutyl ester;
Pentanoic acid, 2-methyl-, 1-methylbutyl ester;
Butyric acid, 2-ethyl-, tert-pentyl ester;
Butyric acid, 2-ethyl-2-methyl-, butyl ester;
Butanoic acid, 3,3-dimethyl-, pentyl ester;
Hexanoic acid, 2-ethyl-3-methyl-, ethyl ester;
Hexanoic acid, 3-methyl-, sec-butyl ester;
Valeric acid, 3,3-dimethyl-, butyl ester;
Pentanoic acid, 3-methyl-, 2-methylbutyl ester;
Hexanoic acid, 1,1-dimethylpropyl ester;
Propanoic acid, 2-methyl-, 5-methylhexyl ester;
Octanoic acid, 2,6-dimethyl-, methyl ester;
Octanoic acid, 2,6-dimethyl-, methyl ester;
Hexanoic acid, 3-(1-methylethyl)-, ethyl ester;
Octanoic acid, 3,7-dimethyl-, methyl ester;
Butanoic acid, 2,2-dimethyl-, pentyl ester;
Octanoic acid, 2,2-dimethyl-, methyl ester;
Butanoic acid, 3-methyl-, 1-methylpentyl ester;
Pentanoic acid, 2-methyl-2-propyl-, ethyl ester;
Octanoic acid, 3,4-dimethyl-, methyl ester;
Octanoic acid, 3,5-dimethyl-, methyl ester;
Butyric acid, 2-ethyl-, 1-ethylpropyl ester;
Hexanoic acid, 2-methyl-, 2-methylpropyl ester;
Pentanoic acid, 1,1-dimethylbutyl ester;
Pentanoic acid, 4-methyl-, 3-methylbutyl ester;
Octanoic acid, 4,6-dimethyl-, methyl ester;
Octanoic acid, 2,7-dimethyl-, methyl ester;
Propanoic acid, 2-methyl-, 1-methylhexyl ester;
Propanoic acid, 2-methyl-, 1-methylhexyl ester;
Propanoic acid, 2-methyl-, 1-methylhexyl ester;
Propanoic acid, 2-methyl-, 1-ethylpentyl ester;
Propanoic acid, 2-methyl-, 1-ethylpentyl ester;
Propanoic acid, 2-methyl-, 1-ethylpentyl ester;
Hexanoic acid, 5-methyl-, tert-butyl ester;
Hexanoic acid, 2-isopropyl-, ethyl ester;
Hexanoic acid, 1,2-dimethylpropyl ester;
Butanoic acid, 2-methyl-, 4-methylpentyl ester;
Butanoic acid, 3-methyl-, 3-methylpentyl ester;
Heptanoic acid, 1,1-dimethylethyl ester;
Butanoic acid, 2,2-dimethylpentyl ester;
Pivalic acid, 1,3-dimethylbutyl ester;
Heptanoic acid, 3,3-dimethyl-, ethyl ester;
Pentanoic acid, 3-methyl-, 3-methylbutyl ester;
Hexanoic acid, 5-methyl-2-(1-methylethyl)-, methyl ester;
Propanoic acid, 2,2-dimethyl-, hexyl ester;
Pentanoic acid, 2-methyl-, 3-methylbutyl ester;
Isobutyric acid, 2,2-dimethylpentyl ester;
Hexanoic acid, 2-methyl-2-propyl-, methyl ester;
Octanoic acid, 2,6-dimethyl-, methyl ester;
Octanoic acid, 3,7-dimethyl-, methyl ester;
Hexanoic acid, 2-ethyl-5-methyl-, ethyl ester;
Octanoic acid, 3,6-dimethyl-, methyl ester;
Hexanoic acid, 2-methyl-, 1-methylpropyl ester;
Hexanoic acid, 2-ethyl-2-methyl-, ethyl ester;
Valeric acid, 2,2-dimethyl-, butyl ester;
Heptanoic acid, 2,2-dimethyl-, ethyl ester;
Pentanoic acid, 2-propyl-, 1-methylethyl ester;
Heptanoic acid, 2-ethyl-2-methyl-, methyl ester;
Hexanoic acid, 4-methyl-, 2-methylpropyl ester;
Valeric acid, 2-methyl-, 1-ethylpropyl ester;
Butanoic acid, 2-ethyl-, 3-methylbutyl ester;
Pentanoic acid, 2-ethyl-4-methyl-, propyl ester;
Heptanoic acid, 5-methyl-, 1-methylethyl ester;
Hexanoic acid, 2,2-dimethylpropyl ester;
Hexanoic acid, 2-ethyl-, 1-methylethyl ester;
Heptanoic acid, 2,3-dimethyl-, ethyl ester;
Octanoic acid, 2,4-dimethyl-, methyl ester;
Heptanoic acid, 3,5-dimethyl-, ethyl ester;
Heptanoic acid, 3,5-dimethyl-, ethyl ester;
Hexanoic acid, 2,2-diethyl-, methyl ester;
Butanoic acid, 2-methyl-, 2-methylpentyl ester;
Butanoic acid, 2-methyl-, 3-methylpentyl ester;
Butanoic acid, 3-methyl-, 4-methylpentyl ester;
Octanoic acid, 2,5-dimethyl-, methyl ester;
Pentanoic acid, 2-methyl-, 2-methylbutyl ester;
Valeric acid, 2,2-diethyl-, ethyl ester;
Heptanoic acid, 2,3-dimethyl-, ethyl ester;
Heptanoic acid, 2,3-dimethyl-, ethyl ester;
Heptanoic acid, 4,6-dimethyl-, ethyl ester;
Valeric acid, 2-isobutyl-4-methyl-, methyl ester;
Valeric acid, 3,4-dimethyl-, sec-butyl ester;
Isobutyric acid, 1,1-diethylpropyl ester;
Propanoic acid, 2,2-dimethyl-, 2-ethylbutyl ester;
Pentanoic acid, 4-methyl-3-(1-methylethyl)-, ethyl ester;
Butanoic acid, 3,3-dimethyl-, 1-methylbutyl ester;
Hexanoic acid, 4-methyl-, 1,1-dimethylethyl ester;
Pentanoic acid, 2-ethyl-2,3-dimethyl-, ethyl ester;
Pentanoic acid, 2,2-dimethyl-, 2-methylpropyl ester;
Pentanoic acid, 1,1,2-trimethylpropyl ester;
Butanoic acid, 2,2-dimethyl-, 3-methylbutyl ester;
Valeric acid, 2,2-dimethyl-, tert-butyl ester;
Heptanoic acid, 3,6,6-trimethyl-, methyl ester;
Hexanoic acid, 2-methyl-, 1,1-dimethylethyl ester;
Butanoic acid, 2-methyl-1-(1-methylethyl)propyl ester;
Propanoic acid, 2,2-dimethyl-, 1,2,2-trimethylpropyl ester;
Pentanoic acid, 2-ethyl-2,4-dimethyl-, ethyl ester;
Butanoic acid, 3-methyl-, 1,3-dimethylbutyl ester;
Butyric acid, 2-ethyl-, neopentyl ester;
Hexanoic acid, 2,2-dimethyl-, 1-methylethyl ester;
Pentanoic acid, 2-ethyl-2-methyl-, 1-methylethyl ester;
Heptanoic acid, 5,6,6-trimethyl-, methyl ester;
Hexanoic acid, 2,2,4-trimethyl-, ethyl ester;
Propanoic acid, 2,2-dimethyl-, 1-methylpentyl ester;
Butanoic acid, 3,3-dimethyl-2-(1-methylethyl)-, ethyl ester;
Hexanoic acid, 3,5,5-trimethyl-, ethyl ester;
Pentanoic acid, 4,4-dimethyl-2-propyl-, methyl ester;
Hexanoic acid, 3-ethyl-2,5-dimethyl-, methyl ester;
Hexanoic acid, 3-ethyl-2,5-dimethyl-, methyl ester;
Hexanoic acid, 2,2,3-trimethyl-, ethyl ester;
Heptanoic acid, 2,2,4-trimethyl-, methyl ester;
Heptanoic acid, 2,2,6-trimethyl-, methyl ester;
Hexanoic acid, 3,3,5-trimethyl-, ethyl ester;
Butyric acid, 2,2,3-trimethyl-, butyl ester;
Pentanoic acid, 2,3-diethyl-3-methyl-, methyl ester;
Butyric acid, 2,2-diethyl-3-methyl-, ethyl ester;
Valeric acid, 2-ethyl-2,4-dimethyl-, ethyl ester;
Propanoic acid, 2-methyl-, 1-ethyl-3-methylbutyl ester;
Butanoic acid, 2-ethyl-2-methyl-, 2-methylpropyl ester;
Butanoic acid, 2-(1,1-dimethylethyl)-3,3-dimethyl-, methyl ester;
Pentanoic acid, 2,4-dimethyl-, 1,1-dimethylethyl ester;
Pentanoic acid, 2,4-dimethyl-, 1,1-dimethylethyl ester;
Pentanoic acid, 2,3,4,4-tetramethyl-, ethyl ester;

Pentanoic acid, 2,3,4,4-tetramethyl-, ethyl ester;
Pentanoic acid, 2,3,4,4-tetramethyl-, ethyl ester;
Pentanoic acid, 2,3,4,4-tetramethyl-, ethyl ester;
Butanoic acid, 3,3-dimethyl-, 1,1-dimethylpropyl ester;
Propanoic acid, 2,2-dimethyl-, 1,1-dimethylbutyl ester;
Propanoic acid, 2-methyl-, 1,1,3-trimethylbutyl ester;
Butyric acid, 2,3-dimethyl-, 1,2-dimethylpropyl ester;
Pentanoic acid, 4,4-dimethyl-2-(1-methylethyl)-, methyl ester;
Butanoic acid, 2,2-dimethyl-, 2,2-dimethylpropyl ester;
Butanoic acid, 3,3-dimethyl-, 2,2-dimethylpropyl ester;
Pentanoic acid, 2,2,4,4-tetramethyl-, ethyl ester;
Pentanoic acid, 2,4-dimethyl-2-(1-methylethyl)-, methyl ester;
Butanoic acid, 2-ethyl-2,3-dimethyl-, 1-methylethyl ester;
Butanoic acid, 2,3-dimethyl-2-(1-methylethyl)-, ethyl ester;
Hexanoic acid, 3,3,5,5-tetramethyl-, methyl ester;
Pentanoic acid, 2-ethyl-3,3,4-trimethyl-, methyl ester;
Pentanoic acid, 3-ethyl-2,4,4-trimethyl-, methyl ester;
Pentanoic acid, 2-(1,1-dimethylethyl)-2-methyl-, methyl ester;
Butanoic acid, 2,2-diethyl-3,3-dimethyl-, methyl ester;
Butanoic acid, 2-ethyl-3-methyl-2-(1-methylethyl)-, methyl ester;
Hexanoic acid, 2,2,4,4-tetramethyl-, methyl ester;
Pentanoic acid, 2,3,4,4-tetramethyl-, ethyl ester;
Butanoic acid, 2-ethyl-2,3,3-trimethyl-, ethyl ester;
Propanoic acid, 2-methyl-, 2-methyl-1-(1-methylethyl)propyl ester;
Butanoic acid, 2,2,3-trimethyl-, 2-methylpropyl ester;
Propanoic acid, 2,2-dimethyl-, 1,1,2-trimethylpropyl ester;
Butanoic acid, 2,3,3-trimethyl-2-(1-methylethyl)-, methyl ester;
Heptanoic acid, 3-ethyl-, ethyl ester.

Preferably, the esters according to the invention have evaporation rates such that the amount evaporated in 30 minutes is between 4.1 mg/cm$^2$ and 24 mg/cm$^2$ (when it is measured on the compound alone, under the conditions defined hereinafter).

The measurement of the volatility of a solvent is described in patent application WO 06/013413, as a function of the amount evaporated in 30 minutes, according to the protocol defined hereinafter:

Measurement of the Rate of Evaporation of a Solvent (Protocol)

15 g of oil or of the mixture of oils to be tested are placed in a crystallizing dish (diameter: 7 cm) placed on a balance that is inside a chamber of about 0.3 m$^3$ with a regulated temperature (25° C.) and a regulated hygrometry (relative humidity 50%). The liquid is allowed to evaporate freely, without stirring it, while providing ventilation with a fan (Papst-Motoren, reference 8550 N, rotating at 2700 rpm) positioned vertically above the crystallizing dish containing the solvent, the vanes facing the crystallizing dish and being 20 cm from the bottom of the crystallizing dish. The mass of oil remaining in the crystallizing dish is measured at regular intervals. The evaporation rates are expressed in mg of oil evaporated per unit of surface area (cm$^2$) and per unit of time (minutes).

By way of indication, the amount by mass of volatile oil evaporated after 30 minutes for certain volatile oils according to this protocol is given hereinafter:
  isododecane: 24 mg/cm$^2$,
  octamethylcyclotetrasiloxane (D4): 18.7 mg/cm$^2$,
  decamethylcyclohexasiloxane (D5): 4.1 mg/cm$^2$.

Preferably, the esters according to the invention have a flash point of between 43 and 100° C., and more particularly between 45 and 80° C. By way of indication, the flash points of isododecane and of the cyclomethicone D5 are 45° C. and 77° C., respectively.

The ester of formula (I) or of formula (II) can be used as sole volatile lipophilic solvent or as a mixture with other additional lipophilic volatile solvents (also known as "oils") which do not correspond to formulae (I) and (II).

In the case of a mixture of volatile solvents, the measuring protocol is the same as that described above.

Equations Used:

Taking 100 mg of a composition comprising i solvents each having an evaporation rate $v_i$ (measured according to the protocol described above), expressed as mg of oil evaporated per unit of surface area (cm$^2$) and per unit of time (minute).

The solvents are introduced into the composition in an initial amount per unit of surface area equal to $m_i(0)$ (expressed in mg per cm$^2$).

For each solvent, the remaining mass per unit of surface area at a time t [$m_i(t)$] can be given by the following equations:

$$m_i(t) = m_i(0) - v_i \cdot t \text{ if } t < \frac{m_i(0)}{v_i}$$

$$m_i(t) = 0 \text{ if } t \geq \frac{m_i(0)}{v_i}$$

The total mass of liquid fatty phase can then be given by the sum of all the individual masses $m_i(t)$ at each of the times:

$$M = \sum_i m_i(t)$$

The calculation is thus performed for a time t=30 minutes.

It will be noted that, in this approach, non-volatile oils are considered to have zero evaporation rates.

According to an advantageous embodiment, when the ester is used as a mixture with other volatile lipophilic solvents, it should be present at least 30%, or better still 50%, by mass of the total sum of the lipophilic volatile solvents.

According to an advantageous embodiment, irrespective of whether or not the ester(s) according to the invention is (are) used as a mixture with other solvents, the ester(s) according to the invention preferably represent(s) at least 2% by weight, or better still at least 5% by weight, relative to the total weight of the composition.

The term "lipophilic" is intended to mean water-immiscible solvents. The lipophilic solvents are defined on the basis of their solubility parameter δa which is given by the following equation:

$$\delta_a = \sqrt{\delta_p^2 + \delta_h^2}$$

where δp and δh are the Hansen solubility parameters calculated using group contributions, according to the reference "Van Krevelen, D. W., Properties of Polymer: Their Correlation with Chemical Structure; Their Estimation and Prediction from Additive Group Contribution. 3rd ed. Elsevier (1990)". The calculations are given in chapter 7 of said work. The equations giving the solubility parameters $\delta_d$, $\delta_p$ and $\delta_h$ are given on page 212 (Hoftyzer & Van Krevelen method). They are calculated from the molar volume of the desired constituent, which is given by Table 7.9, page 215 ($V = \Sigma N_i V_i$) and from the values of $V_i$ appearing in Table 7.3, pages 196-197. The number $N_i$ represents the number of groups i per molecule. The equations also involve parameters $F_{di}$, $F_{pi}$ and $E_{hi}$, which are given by Table 7.8, page 213.

The lipophilic solvents according to the present invention are considered to have values of δa<15 $J^{1/2} \cdot cm^{-3/2}$, better still δa<10 $J^{1/2} \cdot cm^{-3/2}$.

The term "volatile oil" or "volatile solvent" is intended to mean an oil (or nonaqueous medium) capable of evaporating on contact with the skin or with the keratin fibre, and more generally with the keratin material, in less than one hour, at ambient temperature and atmospheric pressure. The volatile oil is a volatile cosmetic oil, that is liquid at ambient temperature, having in particular a non-zero vapour pressure, at ambient temperature and atmospheric pressure, in particular having a vapour pressure ranging from 0.13 Pa to 40 000 Pa ($10^{-3}$ to 300 mmHg), in particular ranging from 1.3 Pa to 13 000 Pa (0.01 to 100 mmHg), and more particularly ranging from 1.3 Pa to 8000 Pa (0.01 to 60 mmHg).

In the context of the present invention, the volatile oils which do not correspond to formulae (I) and (II) and which may be present in the composition are the oils for which the amount evaporated after 30 minutes under the conditions described above is greater than or equal to 0.07 $mg/cm^2$.

Among these volatile oils not in accordance with formulae (I) and (II), mention may be made of cyclic or noncyclic silicone volatile oils, or non-silicone volatile oils, in particular chosen from hydrocarbon-based or fluorinated volatile oils, and mixtures thereof.

Among the "cyclic or noncyclic silicone volatile oils" mention may in particular be made of the linear oils having a viscosity≤6 centistokes ($6\times10^{-6}$ $m^2/s$), and having in particular from 3 to 10 silicon atoms, these silicones optionally comprising one or more alkyl or alkoxy groups containing 1 or 2 carbon atoms. In this category of silicone volatile oils that can be used in the invention, mention may in particular be made of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

The noncyclic silicone volatile oils can also be chosen from linear or branched silicone volatile oils.

The hydrocarbon-based volatile oil not in accordance with formula (I) or (II) can be chosen from hydrocarbon-based volatile oils containing from 8 to 16 carbon atoms, and mixtures thereof, and in particular $C_8$-$C_{16}$ branched alkanes, such as isoalkanes (also known as isoparaffins), isododecane (also known as 2,2,4,4,6-pentamethylheptane), isodecane or isohexadecane, and, for example, the oils sold under the trade names Isopars® or Permethyls®.

Other hydrocarbon-based volatile oils can be chosen from:
1) carbonic acid esters of formula R1-O—CO—O—R2, in which R1 and R2 are identical or different and represent a linear or branched hydrocarbon-based radical, with the proviso that:
when R1 and R2 are linear, they each contain from 1 to 6 carbon atoms, with 6≤R1+R2≤7; and
when R1 and/or R2 are branched, they each contain from 1 to 8 carbon atoms, with 6≤R1+R2≤9.
2) ketones of formula R1-CO—R2 in which R1 and R2 are identical or different and represent a linear or branched hydrocarbon-based radical, with the proviso that:
when R1 and R2 are linear, they each contain from 1 to 8 carbon atoms, with 8≤R1+R2≤9; and
when R1 and/or R2 are branched, they each contain from 1 to 10 carbon atoms, with 9≤R1+R2≤11.
3) ethers of formula R1-O—R2, in which R1 and R2 are identical or different and represent a linear or branched hydrocarbon-based radical, with the proviso that:
when R1 and R2 are linear, they each contain from 1 to 10 carbon atoms, with 10≤R1+R2≤11; and
when R1 and/or R2 are branched, they each contain from 1 to 12 carbon atoms, with 10≤R1+R2≤13.
4) aldehydes of formula R1COH, in which R1 represents a linear or branched hydrocarbon-based radical, with the proviso that:
when R1 is linear, it contains 7 or 8 carbon atoms; and
when R1 is branched, it contains 8 to 10 carbon atoms.

In these various formulae 1) to 4), R1 and R2 (when it exists) are chosen independently of one another and are two distinct radicals, i.e. they are not linked to one another by a covalent bond. Preferably, R1 and R2 are alkyl radicals.

Other hydrocarbon-based volatile oils, such as petroleum distillate, in particular those sold under the name "Shell Solt®" by the company Shell, may be used.

According to a variant of the invention, the composition of the present invention is free of cyclic or noncyclic silicone volatile oils, i.e. comprises less than 0.1% by weight of these cyclic or noncyclic silicone volatile oils, relative to the total weight of the composition.

According to another variant of the invention, the composition is free of cyclic silicone volatile oil, especially octamethylcyclotetrasiloxane, decamethylcyclopentasiloxane or dodecamethylcyclohexasiloxane, and in particular octamethylcyclotetrasiloxane, i.e. comprises less than 0.1% by weight of cyclic silicone oils relative to the total weight of the composition.

Preferably, when the ester of formula (I) or (II) is used as a mixture with other volatile solvents not in accordance with formulae (I) and (II), these other solvents are natural or of natural origin. In general, the various oils of the composition (volatile or non-volatile, and including the esters of formula (I) or (II)), the solid fatty substances or the other ingredients of the composition will preferably be natural or of natural origin.

The "natural" compounds are:
compounds of biological agricultural plant origin or wild-plant origin with carefully thought out sampling,
compounds of agricultural plant origin or originating from the kingdom Protista, compounds of non-fossil mineral origin,
compounds of animal origin, preferably compounds secreted by animals (beeswax).

The compounds "of natural origin" are natural compounds having undergone conversions, it being possible for these conversions to be:
1) conversions which do not modify the composition of the starting material relative to its origin, other than possibly its water content. These conversions generate essentially modifications to the physical appearance of the ingredient relative to its origin. examples of conversions which fall into this category are:
crushing,
milling,
drying,
freeze-drying,
thermal preservation processes (sterilization in a hermetically sealed container, pasteurization),
pressurized preservation processes (Pascalization),
the addition of preserving agents of plant origin being accepted.
2) processes aimed at extracting, in the case of ingredients of plant origin, a given fraction of the plant without breaking covalent chemical bonds, which encompasses the following processes:

expression,
pressing,
flash vacuum-expansion processes,
distillation,
water-extraction processes (decoction, infusion, maceration),
ethanol-extraction processes (including enfleurage),
extraction processes with supercritical $CO_2$,
the above extraction processes using microwave heating,
steam distillation,
purification processes,
purification processes based on the preceding technologies,
purification processes by passing over active charcoal, over oxides or over resin, thermal preservation processes (sterilization in a hermetically sealed container, pasteurization),
winterization or cold clearing processes,
bioconversions applied to starting materials of plant origin and catalysed by non genetically modified organisms, and the original function of which corresponds to the targeted reaction,
pressurized preservation processes (Pascalization) or preservation processes using the addition of preserving agents of plant origin,
genetic extraction processes which do not fall into this category and also irradiation-based preservation processes.

3) in the case of the non-fossil mineral materials, the conversion processes may be the following:
processes aimed at purifying or slightly modifying the starting material without significant modification of its crystalline structure or its composition,
distillation,
purification processes (elimination of heavy metals, of organic compounds, etc.),
ion exchange processes,
purification processes by passing over active charcoal, over oxides or over resin,
thermal preservation processes,
pressurized preservation processes (Pascalization).

4) conversions by chemical process generating a minor modification, and in particular with regard to compounds of plant origin:
extraction with an organic solvent (hexane, fluoro ethers, or the like),
hydrolysis,
esterification,
oxidation using oxygen as oxidant,
olefin hydrogenations,
hydrogenation of acids and of esters,
etherifications,
Guerbet reaction (intermolecular reaction between alcohols similar to a "cooking" process),
and for the ingredients of non-fossil mineral origin: processes for obtaining materials by dissolution/reprecipitation of mineral species resulting in simple or structured oxides (zeolites, mesoporous compounds, etc.).

5) conversions for a functionalization, in particular amination, nitration, silylation, carboxylation using catalysts of mineral or biological origin and also bioconversions by means of genetically modified organisms, the function of which may or may not correspond to the original reaction, and processes that give rise to the synthesis of oxide mixtures.

According to a first embodiment of the invention, a compound is in particular considered to be natural or of natural origin as defined above in points 4) or 5) when the amount by weight of a natural product or product of natural origin is greater than the amount by weight which does not correspond to this definition.

According to a second embodiment, a compound is in particular considered to be natural or of natural origin as defined above in points 4) or 5) when the number of carbon atoms of a natural compound or compound of natural origin is greater than the number of carbon atoms which do not correspond to this definition.

Thus, solvents that are not therefore considered to be natural compounds or compounds of natural origin include certain volatile solvents conventionally used in cosmetic compositions, such as isododecane, which is of mineral fossil origin (derived from petroleum chemistry) or cyclomethicone D5, which is a silicone compound prepared by chemical synthesis processes.

Advantageously, the compositions according to the invention are such that the volatile solvents which are not natural or of natural origin represent less than 20% by mass of the sum of the volatile solvents of the composition.

Preferably, the composition is such that the mixture of said esters and/or of said volatile oils not in accordance with formula (I) or (II) and/or of fatty substances optionally present contains less than 2% by mass of non-natural compounds or compounds which are not of natural origin, relative to the mass of said mixture (it thus being possible for said mixture to be completely free of such compounds).

According to a specific embodiment, when the ester of formula (I) or (II) is used in mixtures with other lipophilic volatile solvents which do not correspond to formula (I) or (II), the mixing must be carried out in such a way that the mixture of volatile solvents, or volatile fatty phase, in the composition according to the invention has an evaporation profile such that the mass of oil(s) evaporated after 30 minutes according to the conditions defined above is between 4.1 $mg/cm^2$ and 24 $mg/cm^2$.

Preferably, the volatile fatty phase comprising the esters according to formula (I) or (II) and, optionally, other volatile oils represents a content ranging from 0.1% to 80% by weight, especially from 1% to 65% by weight, in particular from 10% to 50% by weight, relative to the total weight of the composition.

According to another aspect, a subject of the invention is also the use of the esters of formulae (I) and (II) as volatile solvent for the preparation of a cosmetic composition.

According to another aspect, a subject of the invention is also a cosmetic process for making up and/or caring for keratin materials, comprising at least the step of applying a composition according to the invention to the keratin materials.

Another subject of the invention is a process for preparing such make-up and/or care compositions.

Physiologically Acceptable Medium

The term "physiologically acceptable medium" denotes a medium which is nontoxic and which can be applied to the skin, in particular of the body, the hands, the neck or the face, the lips and/or keratin fibres of human beings. The physiologically acceptable medium is generally suitable for the nature of the support on which the composition must be applied and also for the way in which the composition is intended to be packaged.

Non-Volatile Oils

The composition according to the invention may also comprise at least one non-volatile oil. Said oil may in particular be chosen from non-volatile hydrocarbon-based and/or silicone and/or fluoro oils.

The term "non-volatile oil" is intended to mean an oil that remains on the skin or the keratin fibre, more generally on the keratin material, at ambient temperature and atmospheric pressure, for at least several hours and that in particular has a vapour pressure of less than $10^{-3}$ mmHg (0.13 Pa). A non-volatile oil can also be defined as having an evaporation rate such that, under the conditions defined above, the amount evaporated after 30 minutes is less than 0.07 mg/cm$^2$.

As non-volatile hydrocarbon-based oil, mention may in particular be made of:

hydrocarbon-based oils of plant origin, such as triglycerides consisting of fatty acid esters of glycerol, the fatty acids of which may have chain lengths ranging from $C_4$ to $C_{24}$, it being possible for the latter to be linear or branched, and saturated or unsaturated, such as triglycerides of heptanoic acid or octanoic acid; these oils are in particular wheatgerm oil, sunflower oil, grapeseed oil, sesame oil, maize oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, sesame oil, marrow oil, rapeseed oil, blackcurrant oil, evening primrose oil, millet oil, barley oil, quinoa oil, rye oil, safflower oil, candlenut oil, passionflower oil or musk rose oil; or else caprylic/capric acid triglycerides, for instance those sold by the company Stéarineries Dubois or those sold under the names "Miglyol 810®", "812®" and "818®" by the company Dynamit Nobel;

oils of animal origin, such as mink oil, turtle oil or perhydrosqualene;

synthetic ethers;

linear or branched hydrocarbons of mineral or synthetic origin, such as liquid paraffin or its derivatives, petroleum jelly, polydecenes, hydrogenated polyisobutenes such as Parleam® sold by the company Nippon Oil Fats, and squalene, and mixtures thereof;

esters of a fatty acid, in particular a fatty acid containing from 4 to 22 carbon atoms, and especially of octanoic acid, heptanoic acid, lanolic acid, oleic acid, lauric acid or stearic acid, such as propylene glycol dioctanoate, propylene glycol monoisostearate, polyglyceryl 2-diisostearate or neopentyl glycol diheptanoate;

synthetic esters, for instance oils of formula $R_1COOR_2$ in which $R_1$ represents a linear or branched fatty acid residue containing from 1 to 40 carbon atoms and $R_2$ represents a hydrocarbon-based chain, which is in particular branched, containing from 1 to 40 carbon atoms, on condition that $R_1+R_2$ is $\geq 11$, for instance purcellin oil (cetostearyl octanoate), isononyl isononanoate, $C_{12}$ to $C_{15}$ alkyl benzoate, 2-ethylhexyl palmitate, 2-octyldodecyl stearate, 2-octyldodecyl erucate, isostearyl isostearate, 2-octyldodecyl benzoate, octanoates, decanoates or ricinoleates of alcohols or of polyalcohols, isopropyl myristate, isopropyl palmitate, butyl stearate, hexyl laurate, diisopropyl adipate, 2-ethylhexyl palmitate, 2-hexyldecyl laurate, 2-octyldecyl palmitate, 2-octyldodecyl myristate, 2-diethylhexyl succinate, diisostearyl malate or isododecyl neopentanoate;

hydroxylated esters, such as isostearyl lactate, octyl hydroxystearate, octyldodecyl hydroxystearate, diisostearyl malate, triisocetyl citrate, glyceryl triisostearate or diglyceryl triisostearate; diethylene glycol diisononanoate; and pentaerythritol esters; esters of aromatic acids and of alcohols containing 4 to 22 carbon atoms, in particular tridecyl trimellitate;

fatty alcohols that are liquid at ambient temperature, with a branched and/or unsaturated carbon-based chain containing from 8 to 26 carbon atoms, for instance oleyl alcohol, linoleyl alcohol, linolenyl alcohol, isostearyl alcohol or octyldodecanol; $C_8$-$C_{26}$ higher fatty acids, such as oleic acid, linoleic acid, linolenic acid or isostearic acid;

and mixtures thereof.

The non-volatile silicone oils that can be used in the composition according to the invention may be non-volatile polydimethylsiloxanes (PDMSs), polydimethylsiloxanes comprising alkyl or alkoxy groups, which are pendant and/or at the end of a silicone chain, these groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes or 2-phenylethyl trimethylsiloxy-silicates.

According to one aspect of the invention, the composition is free of non-volatile oil, i.e. comprises less than 0.1% by weight of non-volatile oil relative to the total weight of the composition.

According to another aspect of the invention, the non-volatile oil may be present at a content ranging from 0.1% to 60% by weight, especially ranging from 0.5% to 500% by weight, and in particular ranging from 1% to 40% by weight, relative to the total weight of the composition.

Solid Fatty Substances

The composition according to the invention may comprise, in particular when it is a lipstick or a foundation, at least one fatty substance that is solid at ambient temperature and at atmospheric pressure; it may be chosen from waxes, pasty fatty substances and gums, and mixtures thereof. This solid fatty substance may be present at a content ranging from 0.01% to 60%, especially from 0.1% to 50%, and in particular from 0.1% to 40% by weight, relative to the total weight of the composition.

Thus, the composition according to the invention may comprise at least one fatty compound that is pasty at ambient temperature.

For the purpose of the invention, the term "pasty fatty substance" is intended to mean fatty substances with a melting point ranging from 20 to 55° C., in particular 25 to 45° C., and/or a viscosity at 40° C. ranging from 0.1 to 40 Pa·s (1 to 400 poises), in particular 0.5 to 25 Pa·s, measured using a Contraves TV or Rheomat 80 viscometer, equipped with a spindle rotating at 60 Hz. Those skilled in the art can select the spindle for measuring the viscosity from the spindles MS-r3 and MS-r4, on the basis of their general knowledge, so as to be able to perform the measurement of the pasty compound tested.

More particularly, these fatty substances may be hydrocarbon-based compounds, optionally of polymeric type; they may also be chosen from silicone compounds; they may also be in the form of a mixture of hydrocarbon-based and/or silicone compounds. In the case of a mixture of various pasty fatty substances, hydrocarbon-based pasty compounds (mainly containing carbon and hydrogen atoms and possibly ester groups) are preferably used in major proportion.

Among the pasty compounds that may be used in the composition according to the invention, mention may be made of lanolins and lanolin derivatives, such as acetylated lanolins, oxypropylenated lanolins or isopropyl lanolate, with a viscosity of from 18 to 21 Pa·s, preferably 19 to 20.5 Pa·s, and/or a melting point of 30 to 55° C. and mixtures thereof. Use may also be made of esters of fatty acids or of fatty alcohols, in particular those containing 20 to 65 carbon atoms (melting point of the order of 20 to 35° C. and/or viscosity at 40° C. ranging from 0.1 to 40 Pa·s), for instance triisostearyl citrate or cetyl citrate; arachidyl propionate; polyvinyl laurate; cholesterol esters, for instance triglycerides of plant origin such as hydrogenated plant oils, viscous polyesters, and mixtures thereof. Triglycerides of plant origin that may be used include hydrogenated castor oil derivatives, such as "Thixinr®" from Rheox.

Mention may also be made of pasty silicone fatty substances such as high-molecular-weight polydimethylsiloxanes (PDMSs), and in particular those with pendant chains of the alkyl or alkoxy type containing from 8 to 24 carbon atoms, and a melting point of 20-55° C., for instance stearyl dimethicones, in particular those sold by the company Dow Corning under the trade names DC2503® and DC25514®, and mixtures thereof.

The pasty fatty substance may be present in the composition according to the invention at a content ranging from 0.01% to 50% by weight, especially ranging from 0.1% to 45% by weight, and in particular ranging from 0.2% to 30% by weight, relative to the total weight of the composition.

In the context of the present invention, the term "wax" is generally intended to mean a lipophilic compound that is solid at ambient temperature (25° C.), deformable or nondeformable, with a reversible solid/liquid change of state, having a melting point of greater than or equal to 30° C., which may be up to 200° C., and in particular up to 120° C.

By bringing the wax to the liquid state (melting), it is possible to render it miscible with oils and to form a microscopically homogeneous mixture, but when returning the temperature of the mixture to ambient temperature, recrystallization of the wax from the oils in the mixture is obtained.

In particular, the waxes suitable for the invention may have a melting point of greater than or equal to 45° C., and in particular greater than or equal to 55° C.

For the purpose of the invention, the melting point corresponds to the temperature of the most endothermic peak observed by thermal analysis (DSC) as described in ISO standard 11357-3; 1999. The melting point of the wax can be measured using a differential scanning calorimeter (DSC), for example the calorimeter sold under the name "MDSC 2920" by the company TA Instruments.

The measurement protocol is the following:

A sample of 5 mg of wax placed in a crucible is subjected to a first increase in temperature ranging from −20° C. to 100° C., at a heating rate of 10° C./minute, and is then cooled from 100° C. to −20° C. at a cooling rate of 10° C./minute, and, finally, subjected to a second increase in temperature ranging from −20° C. to 100° C. at a heating rate of 5° C./minute. During the second increase in temperature, the variation in the difference in power absorbed by the empty crucible and by the crucible containing the wax sample is measured as a function of temperature. The melting point of the compound is the value of the temperature corresponding to the top of the peak of the curve representing the variation in the difference in power absorbed as a function of temperature.

By way of waxes that may be used according to the invention, mention may be made of:

waxes of animal origin, such as beeswax, lanolin wax and lanolin derivatives, plant-waxes such as carnauba wax, candelilla wax, ouricury wax, Japan wax, cocoa butter, cork fibre wax or sugarcane wax, mineral waxes, for example paraffin wax, petroleum jelly wax, lignite wax, microcrystalline waxes or ozokerites, synthetic waxes, among which are polyethylene waxes and waxes obtained by Fisher-Tropsch synthesis, silicone waxes, in particular substituted linear polysiloxanes; mention may, for example, be made of silicone polyether waxes, alkyl dimethicones or alkoxy dimethicones containing from 16 to 45 carbon atoms, alkyl methicones such as the $C_{30}$-$C_{45}$ alkyl methicone sold under the trade name "AMS C 30" by Dow Corning, hydrogenated oils that are solid at 25° C., such as hydrogenated castor oil, hydrogenated jojoba oil, hydrogenated palm oil, hydrogenated tallow or hydrogenated coconut oil, and fatty esters that are solid at 25° C., such as the $C_{20}$-$C_{40}$ alkyl stearate sold under the trade name "Kester Wax K82H" by the company Koster Keunen, and/or mixtures thereof.

Preferably, polyethylene waxes, microcrystalline waxes, carnauba waxes, hydrogenated jojoba oil, candelilla waxes, beeswaxes and/or mixtures thereof will be used.

Aqueous and/or Water-Soluble Phase

The composition according to the invention may also comprise at least one aqueous phase containing water. The water may be a floral water such as cornflower water and/or a mineral water such as eau de Vittel, eau de Lucas or eau de La Roche Posay and/or a spring water.

The aqueous phase may also comprise organic solvents that are water-miscible (at 25° C.), for instance primary alcohols such as ethanol and isopropanol, glycols such as glycerol, propylene glycol, butylene glycol, dipropylene glycol, diethylene glycol, glycol ethers, $C_1$ to $C_4$ alkyl ethers of mono-, di- or tripropylene glycol, or mono-, di- or triethylene glycol, and mixtures thereof.

The composition may be an anhydrous composition, i.e. a composition containing less than 2% by weight of water, or even less than 0.5% of water, in particular free of water, the water not being added during the preparation of the composition, but corresponding to the residual water introduced by the ingredients mixed in.

Particulate Phase

The composition of the invention may also comprise, in particular when it is a lipstick or a foundation, an additional particulate phase that may be present in a proportion of from 0.01% to 50% by weight, especially from 0.01% to 40% by weight, and in particular from 0.05% to 30% by weight, relative to the total weight of the composition.

The term "particulate phase" is intended to mean preferably pigments and/or pearlescent agents and/or additional fillers, and/or mixtures thereof.

According to an embodiment, the composition of the invention comprises at least a pigment.

The term "pigments" should be understood to mean white or coloured, mineral or organic particles that are insoluble in the liquid hydrophilic phase and are intended to colour and/or opacify the composition. The term "fillers" should be understood to mean colourless or white, mineral or synthetic, lamellar or non-lamellar particles. The term "pearlescent agents" should be understood to mean iridescent particles, in particular produced by certain molluscs in their shell or alternatively which are synthesized.

The pigments may be present in the composition in a proportion of from 0.01% to 25% by weight, in particular from 0.01% to 20% by weight, and especially from 0.02% to 15% by weight, relative to the weight of the composition.

As mineral pigments that may be used in the invention, mention may be made of titanium oxide, zirconium oxide or cerium oxide and also zinc oxide, iron oxide or chromium oxide, ferric blue, manganese violet, ultramarine blue and chromium hydrate. Among the organic pigments that may be used in the invention, mention may be made of carbon black, the D & C pigments and lakes based on cochineal carmine, barium, strontium, calcium, or aluminium, or else the diketo pyrrolopyrroles (DPP) described in documents EP-A-542669, EP-A-787730, EP-A-787731 and WO-A-96/08537.

The pearlescent agents may be present in the composition in a proportion of from 0.01% to 25% by weight, especially from 0.01% to 15% by weight, and in particular from 0.02% to 10% by weight, relative to the total weight of the composition.

The pearlescent pigments may be chosen from white pearlescent pigments such as mica coated with titanium or with bismuth oxychloride, coloured pearlescent pigments such as titanium mica with iron oxides, titanium mica in particular with ferric blue or with chromium oxide, titanium mica with an organic pigment of the type mentioned above, and also pearlescent pigments based on bismuth oxychloride.

According to an embodiment, the composition of the invention comprises at least a filler.

The additional fillers may be present in a proportion of from 0.01% to 50% by weight, especially from 0.01% to 40% by weight, and in particular from 0.02% to 30% by weight, and even more particularly from 0.02% to 20% by weight, relative to the total weight of the composition.

They may in particular be spherical fillers such as, for example, talc, zinc stearate, mica, kaolin, polyamide (Nylon®) powders (Orgasol® from Atochem), polyethylene powders, tetrafluoroethylene polymer (Teflon®) powders, starch, boron nitride, polymeric microspheres such as those made of polyvinylidene chloride/acrylonitrile, for instance Expancel® (Nobel Industrie), or of acrylic acid copolymers (Polytrap® from the company Dow Corning), silicone resin microbeads (Tospearls® from Toshiba, for example), and elastomeric organopolysiloxanes.

The composition may also comprise water-soluble or liposoluble dyes at a content ranging from 0.01% to 6% by weight, relative to the total weight of the composition, in particular ranging from 0.01% to 3% by weight. The liposoluble dyes are, for example, Sudan Red, DC Red 17, DC Green 6, β-carotene, soybean oil, Sudan Brown, DC Yellow 11, DC Violet 2, DC Orange 5, and quinoline yellow. The water-soluble dyes are, for example, beetroot juice and methylene blue.

Dyestuff

The composition according to the invention preferably comprises at least one dyestuff. The term "dyestuff" is intended to mean pigments and/or dyes and/or pearlescent agents, and/or mixtures thereof, as defined above.

The dyestuffs may be present in the composition in an amount ranging from 0.01% to 50% by weight, relative to the total weight of the composition, preferably from 0.01 to 30% by weight.

Additives

The composition according to the invention may also comprise any of the ingredients conventionally used in the fields concerned, and more especially in the cosmetics and dermatological field. These ingredients may in particular be chosen from polymers, in particular film-forming polymers, fixing polymers; surfactants; hair conditioners; opacifiers; fragrances; thickeners; gelling agents; hair dyes; silicone resins; silicone gums; preserving agents; antioxidants; active cosmetic agents; sunscreens; pH stabilizers; vitamins; moisturizers; antiperspirants; deodorants; self-tanning compounds, and mixtures thereof. The amounts of these various ingredients are those conventionally used in the fields concerned, and for example from 0.01% to 20% of the total weight of the composition.

Of course, those skilled in the art will take care to select this or these optional additional compound(s), and/or the amount thereof, in such a way that the advantageous properties of the composition according to the invention are not, or not substantially, impaired by the addition considered.

The composition of the invention may be obtained according to the preparation processes conventionally used in cosmetics or in dermatology.

The following examples are given by way of illustration and do not limit the invention.

Formulation

The composition according to the invention may be in the form of a liquid, a paste, a solid, a foam or a spray. It may be an emulsion, in particular a direct or inverse emulsion, or else an anhydrous composition. It may also be in a two-phase form.

The composition finds a specific application as a body or facial care composition, a body or facial cleansing composition such as a shower gel, a bath gel or a make-up remover; a body or facial make-up composition such as a foundation, a lipstick, a lipcare product, a nailcare product, a mascara or an eyeliner; a fragrancing composition; a hair composition such as a hair dye composition or a composition for permanently reshaping the hair; an antisun composition; a deodorant composition; a hair cleansing or haircare composition such as a shampoo or a rinse-out or leave-in conditioner, a rinse-out composition to be applied before or after dyeing, bleaching, permanent-waving or hair straightening, or alternatively between the two steps of a permanent-waving or hair-straightening operation; a hair composition for holding the hairstyle, such as a styling lacquer, a gel, mousse or spray.

In particular, the composition according to the invention can be used for making up and/or caring for the skin, the lips and/or the keratin fibres of a human being.

According to a preferred aspect of the invention, the composition is in the form of lipsticks or complexion products, especially of the foundation type, or of a mascara.

When the composition according to the invention is of the mascara type, it may be applied uniformly or nonuniformly to the surface of the eyelashes, as a single coat or in the form of several superimposed coats. The composition according to the invention may then be more particularly intended for a mascara product comprising a reservoir, containing at least said mascara composition, and a system for applying said composition to the keratin fibres, for instance the eyelashes.

According to one aspect of the invention, this composition is in the form of a product cast as a stick or a dish, for instance lipsticks or lip balms, cast foundations, concealer products, complexion "correctors" and/or "enhancers" and eyeshadows or face powders.

For the purpose of the present invention, the term "cast composition" is intended to mean any cosmetic composition not having the capacity to flow under the action of its own weight, as opposed to "fluid" compositions.

These compositions may, where appropriate, have a pasty appearance at ambient temperature (25° C.). Thus, a cosmetic composition according to the invention may have a melting point or a thermal transition temperature such as a softening point of greater than 25° C., which may especially range from 25 to 85° C., or even from 30 to 60° C., and in particular from 30 to 45° C., and/or a hardness that may range from 0.001 to 0.5 MPa, and especially from 0.005 to 0.4 MPa.

The compositions according to this aspect of the invention, i.e. of cast type, have hardnesses, in particular when they are in stick form.

The aim of the examples which follow is to illustrate the subject of the present invention in a nonlimiting manner. The amounts are given as percentage by mass.

EXAMPLE 1

Foundation in the form of a water-in-oil emulsion having the following composition:

| | |
|---|---|
| Cetyl dimethicone copolyol (Abil EM 90 from the company Goldschmidt) | 3 g |
| Isostearyl diglyceryl succinate (Imwitor 780K from the company Condea) | 0.6 g |
| Ethyl hexanoate (21550, Fluka ®) | 23.58 g |
| Mixture of pigments (hydrophobic iron oxides and titanium oxides) | 10 g |
| Bentone | 1.6 g |
| Polyamide powder (Nylon-12 from Dupont de Nemours) | 8 g |
| Magnesium sulphate | 0.7 g |
| Preserving agent | 0.45 g |
| Fragrance | 0.5 g |
| Water | qs 100 g |

EXAMPLE 2

Oil-in-water foundation having the following composition:

| | |
|---|---|
| Hexyl acetate (148500010, AcrosOrganics ®) | 11 g |
| Hydrogenated polyisobutene (Parleam, NOF Corporation) | 5 g |
| 2-Ethylhexyl palmitate | 11 g |
| Glyceryl isostearate | 4 g |
| Stearic acid | 2 g |
| Triethanolamine | 1 g |
| Polyamide powder (Nylon-12 from Dupont de Nemours) | 5 g |
| Mixture of pigments (iron oxides and titanium oxides) | 10 g |
| Carboxymethylcellulose | 0.2 g |
| Propylene glycol | 5 g |
| Glycerol | 2 g |
| Fragrance | 0.5 g |
| Preserving agents | 0.4 g |
| Water | qs 100 g |

EXAMPLE 3

Lipstick having the following composition:

| | |
|---|---|
| Polyethylene wax (Performalene 655, New Phase Technologies) | 15 g |
| Butyl butanoate (259590010, AcrosOrganics ®) | 70 g |
| Methyl octanoate | 9 g |
| DC Red No. 7 Calcium Lake (pigment) | 6 g |

EXAMPLE 4

Care cream having the following composition:

| Fatty phase | |
|---|---|
| Mixture of glyceryl monostearate and of polyethylene glycol stearate 100 EO (50/50 by weight) (Arlacel 165 from the company ICI) | 2.5 g |
| Stearyl alcohol | 0.5 g |
| Stearic acid | 1 g |
| Hydrogenated polyisobutene (Parleam, NOF Corporation) | 9 g |
| Octyl formate | 4.2 g |

| Aqueous phase | |
|---|---|
| Crosslinked polyacrylic acid (Carbopol 980) | 1 g |
| Triethanolamine | 0.03 g |
| Preserving agent | 0.3 g |
| Water | qs 100 g |

EXAMPLE 5

Make-up remover having the following composition:

| | |
|---|---|
| Isopropyl palmitate | 8 g |
| 1-Methylethyl 4-methylhexanoate | 8 g |
| Stearyl alcohol | 8 g |
| Sucrose stearate | 2 g |
| Stearic acid | 0.3 g |
| Sodium hydroxide | 0.06 g |
| Glycerol | 5 g |
| Carbopol | 0.2 g |
| Water | qs 100 g |

EXAMPLE 6

Spray deodorant having the following composition:

| | |
|---|---|
| Pentyl butanoate (W205915-1KG, Sigma-Aldrich ®) | 33 g |
| PPG-14 butyl ether (Ucon Fluid AP - Amerchol) | 10 g |
| Hydrogenated castor oil (Cutina HR - Cognis) | 4 g |
| Talc | 2 g |
| Aluminium hydrochloride (Micro Dry - Reheis) | 20 g |
| Stearyl alcohol | 14 g |
| PEG-8 distearate (PEG 400 distearate - Stéarineries Dubois) | 2 g |
| C12-15 alkyl benzoate (Finsolv TN - Witco) | 15 g |

EXAMPLE 7

Roll-on deodorant (emulsion) having the following composition:

| | |
|---|---|
| Aluminium hydrochloride (50% solution) (Chlorhydrol 50% USP) | 40 g |
| Steareth 21 (Brij 721 - ICI) | 2 g |
| Steareth 2 (Brij 2 - ICI) | 2 g |
| PPG 15 stearyl ether (Arlamol E - ICI) | 1.5 g |
| Heptyl formate | 3.5 g |
| Water | qs 100 g |

EXAMPLE 8

Anhydrous antiperspirant aerosol having the following composition:

| | |
|---|---|
| Stearalkonium bentonite sold under the name Tixogel MP250 by Sud-Chemie Rheologicals, United Catalysts Inc. | 0.5 g |
| Aluminium hydrochloride | 7 g |
| Isobutane | 80 g |
| Triethyl citrate | 1.4 g |
| Isopropyl palmitate | 3 g |
| Pentyl propanoate (269470010, AcrosOrganics ®) | 8.1 g |

EXAMPLE 9

Suncream having the following composition:

| | |
|---|---|
| Stearic acid | 0.95 g |
| Glyceryl stearate (and) PEG-100 stearate | 2.00 g |
| Cetyl alcohol (and) myristyl alcohol (and) stearyl alcohol | 0.50 g |
| Dimethicone | 0.50 g |
| Phenoxyethanol (and) methylparaben (and) ethylparaben (and) propylparaben (and) isobutylparaben (and) butylparaben | 1.00 g |
| $C_{12}$-$C_{15}$ alkyl benzoate | 8.00 g |
| Ethylhexyl cocoate | 2.00 g |
| Octocrylene | 7.00 g |
| Ethylhexyl triazone | 1.00 g |
| Butyl methoxydibenzoylmethane | 3.50 g |
| Triethanolamine | 0.50 g |
| Glycerol | 4.00 g |
| Methylparaben (and) butylparaben (and) ethylparaben (and) isobutylparaben (and) propylparaben | 0.25 g |
| Disodium EDTA | 0.10 g |
| Water | 52.10 g |
| Carbomer | 0.30 g |
| Potassium cetyl phosphate | 1.00 g |
| Triethanolamine | 0.30 g |
| Titanium dioxide (and) aluminium hydroxide (and) stearic acid | 5.00 g |
| Hexyl acetate (148500010, AcrosOrganics ®) | 10.00 g |

EXAMPLE 10

Hairspray in a pump dispenser, having the following composition:

| | |
|---|---|
| Octylacrylamide/acrylates/butylaminoethyl methacrylate amphoteric polymer (Amphomer ®, National Starch) | 6 g of AM |
| Methyl heptanoate | 3 g |
| Ethanol | qs 100 g |

What is claimed is:

1. A make-up composition comprising, in a physiologically acceptable medium, at least one dyestuff, at least one volatile ester selected from the group consisting of:
   pentyl propanoate,
   ethyl hexanoate,
   heptyl formate,
   butyl butanoate,
   methyl heptanoate,
   hexyl acetate,
   propyl pentanoate,
   ethyl heptanoate,
   methyl octanoate,
   heptyl acetate,
   octyl formate,
   hexyl propanoate,
   pentyl butanoate,
   butyl pentanoate,
   propyl hexanoate,
   1-methylethyl hexanoate,
   2-pentyl butyrate,
   isoamyl butyrate,
   isobutyl isovalerate,
   at least one non-volatile hydrocarbon based oil present in an amount ranging from 0.1 to 60%, by weight relative to the total weight of the composition; and
   optionally at least one volatile oil which differs from the at least one volatile ester,
   wherein said at least one volatile ester is present in an amount of 30% to 100%, by weight relative to the total weight of the volatile oils in said make-up composition, and
   wherein said make-up composition is anhydrous.

2. A make-up composition comprising, in a physiologically acceptable medium, at least one dyestuff, at least one volatile ester chosen from:
   ethyl hexanoate,
   methyl heptanoate,
   ethyl heptanoate,
   methyl octanoate,
   propyl hexanoate,
   1-methylethyl hexanoate,
   1-methylethyl heptanoate,
   1-methylethyl 4-methylhexanoate,
   at least one non-volatile hydrocarbon based oil present in an amount ranging from 0.1 to 60%, by weight relative to the total weight of the composition; and
   optionally at least one volatile oil not in accordance with the volatile ester species above,
   wherein said at least one volatile ester is present in an amount of 30% to 100%, by weight relative to the total weight of the volatile oils in said make-up composition, and
   wherein said make-up composition is anhydrous.

3. The make-up composition according to claim 1, wherein said at least one volatile oil is of natural origin.

4. The make-up composition according to claim 1, wherein at least one of said at least one volatile oil is non-natural, said at least one non-natural volatile oil representing less than 20% by mass of the total sum of the volatile oils of the composition.

5. The make-up composition according to claim 1, further comprising at least one fatty substance not in accordance with said at least one volatile ester, wherein a mixture of said at least one volatile ester, and said at least one fatty substance and/or said volatile oil contains less than 2% by weight of non-natural compounds or compounds that are not of natural origin, relative to the weight of said mixture.

6. The make-up composition according to claim 3, wherein said at least one volatile oil has an evaporation rate such that the amount evaporated in 30 minutes ranges from 4.1 mg/cm$^2$ to 24 mg/cm$^2$.

7. The make-up composition according to claim 1, wherein said at least one volatile ester is present in an amount of 2% or more by weight, relative to the total weight of the composition.

8. The make-up composition according to claim 1, wherein the composition is in the form of a liquid, a paste, a solid, a foam, or a spray.

9. The make-up composition according to claim 1, wherein the composition is in the form of a body or facial make-up composition.

10. The make-up composition according to claim 9, wherein said body or facial make-up composition is chosen from foundations, lipsticks, lipcare products, nailcare products, mascaras, and eyeliners.

11. The make-up composition according to claim 1, wherein the composition is in the form of a product cast as a stick or a dish.

12. The make-up composition according to claim 11, wherein said product cast is chosen from lipsticks, lip balms, cast foundations, concealer products, complexion correctors, complexion enhancers, eyeshadows, and face powders.

13. The make-up composition according to claim 1, wherein said at least one non-volatile oil is chosen from natural oils.

14. The make-up composition according to claim 1, wherein the composition further comprises at least one fatty substance that is solid at ambient temperature and atmospheric pressure.

15. The make-up composition according to claim 14, wherein the at least one fatty substance is chosen from waxes, pasty fatty substances, and gums.

16. The make-up composition according to claim 1, wherein the composition further comprises at least one particulate phase chosen from pigments, fillers, and pearlescent agents.

17. The make-up composition according to claim 1, wherein the composition is in the form of a stick composition or a cast composition.

18. The make-up composition according to claim 1, wherein the composition comprises at least one additive chosen from polymers; surfactants; hair conditioners; pearlescent agents; opacifiers; organic solvents; thickeners; gelling agents; waxes; pasty products; hair dyes; silicone resins; silicone gums; preserving agents; antioxidants; active cosmetic agents; sunscreens; pH stabilizers; vitamins; moisturizers; antiperspirants; deodorants; and self-tanning compounds.

19. A cosmetic process for making up and caring for the skin, lips, and/or keratin fibres, comprising:
applying the make-up composition of claim 1.

20. The make-up composition according to claim 1, wherein said at least one volatile ester is 1-methylethyl hexanoate.

21. The make-up composition according to claim 1, wherein said at least one volatile ester is pentyl propanoate.

22. The make-up composition according to claim 1, wherein said at least one volatile ester is ethyl hexanoate.

23. The make-up composition according to claim 1, wherein said at least one volatile ester is heptyl formate.

24. The make-up composition according to claim 1, wherein said at least one volatile ester butyl butanoate.

25. The make-up composition according to claim 1, wherein said at least one volatile ester is methyl heptanoate.

26. The make-up composition according to claim 1, wherein said at least one volatile ester is propyl pentanoate.

27. The make-up composition according to claim 1, wherein said at least one volatile ester is ethyl heptanoate.

28. The make-up composition according to claim 1, wherein said at least one volatile ester is methyl octanoate.

29. The make-up composition according to claim 1, wherein said at least one volatile ester is octyl formate.

30. The make-up composition according to claim 1, wherein said at least one volatile ester is hexyl propanoate.

31. The make-up composition according to claim 1, wherein said at least one volatile ester is propyl hexanoate.

\* \* \* \* \*